United States Patent
Coop et al.

(10) Patent No.: US 7,838,556 B2
(45) Date of Patent: Nov. 23, 2010

(54) ETHERS OF 3-HYDROXYPHENYLACETIC ACID AS SELECTIVE GAMMA-HYDROXYBUTYRIC ACID RECEPTOR LIGANDS

(75) Inventors: Andrew Coop, Columbia, MD (US); Maharaj K. Ticku, San Antonio, TX (US); Charles P. France, San Antonio, TX (US)

(73) Assignees: University of Maryland, Baltimore, Baltimore, MD (US); Board of Regents, The University of Texas System, Austin, TX (US)

( * ) Notice: Subject to any disclaimer, the term of this patent is extended or adjusted under 35 U.S.C. 154(b) by 582 days.

(21) Appl. No.: 11/707,120

(22) Filed: Feb. 16, 2007

(65) Prior Publication Data

US 2007/0197650 A1    Aug. 23, 2007

Related U.S. Application Data

(60) Provisional application No. 60/774,619, filed on Feb. 21, 2006.

(51) Int. Cl.
*A01N 37/00* (2006.01)
*A01N 37/10* (2006.01)
*A61K 31/19* (2006.01)

(52) U.S. Cl. ...................... 514/557; 514/568
(58) Field of Classification Search .............. 514/557, 514/568
See application file for complete search history.

(56) References Cited

U.S. PATENT DOCUMENTS

| 4,062,895 | A | * | 12/1977 | Marshall ............... 568/638 |
| 4,738,985 | A | | 4/1988 | Kluger et al. |
| 4,983,632 | A | | 1/1991 | Gessa et al. |
| 5,380,937 | A | | 1/1995 | Koehler et al. |
| 5,990,162 | A | | 11/1999 | Scharf |
| 6,204,245 | B1 | | 3/2001 | Siegel et al. |
| 6,436,998 | B1 | | 8/2002 | Cacciaglia et al. |
| 6,472,431 | B2 | | 10/2002 | Cook et al. |
| 6,623,730 | B1 | | 9/2003 | Williams et al. |
| 6,770,784 | B2 | | 8/2004 | Cacciaglia et al. |
| 6,780,889 | B2 | | 8/2004 | Cook et al. |

OTHER PUBLICATIONS

Pharmaceutical Dosage Forms, vol. 2; Tablets—Lieberman, Herbert A.; New York, Dekker, Inc. 1990.*
Chen, Weibin et. al.; Bioorganic & Medicinal Chemistry Letters 15 (2005) 3201-3202.*
Chen et al, *Bioorganic & Medicinal Chemistry Letters*, 15:3201-3202 (2005).
Guin Ting Wong et al, *Trends in Pharmacological Sciences*, 25(1):29-34 (2004).
Nicholson et al, *Drug and Alcohol Dependence*, 63:1-22 (2001).
Bernasconi et al, *TiPS*, 20:135-141 (1999).
Carai et al, *European Journal of Pharmacology*, 428:315-321 (2001).
Cammalleri et al, *Neurophyschopharmacology*, 27(6):960-969 (2002).
Wu et al, *The Journal of Pharmacology and Experimental Therapeutics*, 305(2):675-679 (2003).
Bourguignon et al, *Alcohol*, 20:227-236 (2000).
Waszkielewicz et al, *Polish Journal of Pharmacology*, 56:43-49 (2004).
Macias et al, *Bioorganic and Medicinal Chemistry*, 12:1643-1647 (2004).
Carter et al, *The Journal of Pharmacology and Experimental Therapeutics*, 313(3):1314-1323 (2005).
Renaud et al, *J. Med. Chem.*, 48:364-379 (2005).
Mehta et al, *The Journal of Pharmacology and Experimental Therapeutics*, 299(3):1148-1153 (2001).
Wilson, *HSC NEWS, News Releases*, vol. XXXVIII, Issue 47 (Nov. 22, 2005).
"m-Hydroxyphenylacetic Acid", ChemFinder.com, Database & Internet Searching (Jan. 8, 2006).

* cited by examiner

*Primary Examiner*—Yong S Chong
(74) *Attorney, Agent, or Firm*—Morgan, Lewis & Bockius LLP

(57) ABSTRACT

The present invention generally relates to pharmaceutical compositions comprising ethers of 3-hydroxyphenylacetic acid. The present invention also relates to therapeutic uses of the ethers of 3-hydroxyphenylacetic acid. The ethers of 3-hydroxyphenylacetic acid have the chemical structural of formula (I):

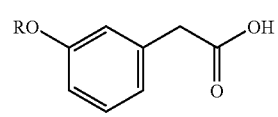

Formula (I)

where R is an aromatic or arylalkyl substituent.

1 Claim, 2 Drawing Sheets

(1) GHB     (2) GABA     (3) 3-chloropropanoic acid

GHB
1 R=H

Ethers of GHB
4 R=Ph(CH$_2$)$_3$
5 R=Ph(CH$_2$)$_2$
6 R=Ph(CH$_2$)
8 R=Ph- 3-hydroxyphenylacetic acid
7 R=H Ethers of 3-hydroxyphenylacetic acid
9 R=Ph(CH$_2$)$_3$
10 R=Ph(CH$_2$)$_2$
11 R=Ph(CH$_2$)
12 R=Ph

ETHERS OF 3-HYDROXYPHENYLACETIC ACID AS SELECTIVE GAMMA-HYDROXYBUTYRIC ACID RECEPTOR LIGANDS

CROSS REFERENCE TO RELATED APPLICATIONS

This application claims priority from U.S. Provisional Application Ser. No. 60/774,619, filed Feb. 21, 2006; the entire disclosure of which is incorporated herein by reference.

STATEMENT REGARDING FEDERALLY SPONSORED RESEARCH OR DEVELOPMENT

Research related to this invention was supported in part by the U.S. Government under grant number R01 DA-14986 awarded by National Institute on Drug Abuse/National Institute of Health. Therefore, the U.S. Government may have certain rights in this invention.

BACKGROUND OF THE INVENTION

Gamma-hydroxybutyric acid (GHB) is a therapeutic and a purported neurotransmitter (Nicholson et al, *Drug Alcohol Depend.*, 63:1 (2001)). GHB is also known as 4-hydroxybutyrate and sodium oxybate. While there are many beneficial uses for GHB, GHB is also included in a class of drugs that have been abused, for example in cases of "date rape" and as an intoxicant.

GHB has a complex mechanism of action in vivo due to direct actions at GHB receptors and at $GABA_B$ receptors. In addition to being an agonist at $GABA_B$ receptors, GHB is rapidly metabolized to gamma-aminobutyric acid (GABA) (Bernasconi et al, *Trends Pharmacol. Sci.*, 20:135 (1999)), resulting in GABAergic activity in vivo (Carai et al, *Eur. J. Pharmacol.*, 428:315 (2001); and Cammalleri et al, *Neuropsychopharmacology*, 27:960 (2002)).

To allow for the separation of actions mediated through GHB receptors from those mediated through the GABA system, there is a need in the art to develop potent and selective GHB agonists, which do not have affinity for GABA receptors and which are not converted to GABA active compounds through metabolism.

Other researchers have prepared GHB NCEs, but all possess GABA activity or the potential to be metabolized to GABAergic agents. Wu et al have reported the developement of tertialy alcohol derivitives of GHB, which can not be metabolized to GABA-active compounds. Wu et al, *J. Pharmacol. Exp. Ther.*, 675:305 (2003). However, there continues to be a need for high affinity metabolically-stable analogs of GHB that have little or no affinity for GABA receptors.

BRIEF SUMMARY OF THE INVENTION

The present invention relates to pharmaceutical compositions comprising ethers of 3-hydroxyphenylacetic acid. The present invention also relates to therapeutic uses of the ethers of 3-hydroxyphenylacetic acid.

GHB interacts with GHB receptors with micromolar affinity and also acts at GABA receptors. GHB is also metabolized to GABA, thus again acting at GABA receptors. The 3-ethers of 3-hydroxyphenylacetic acid of the present invention have high affinity at GHB sites, no significant affinity at GABA receptors, and are not expected to be rapidly metabolized to GABAergic ligands.

The inventive compounds lack the GABA affinity, and thus allow for a therapeutic that acts cleanly through GHB receptors.

It has been shown that the hydrogen of the alcohol of GHB is not essential for affinity at GHB receptors, and that only a hydrogen bond accepting group is required for affinity at GHB receptors (Bourguignon et al, *Alcohol*, 20:227 (2000); Waszkielewicz et al, *Pol. J. Pharmacol.* 56:43 (2004); and Macias et al, *Bioorg. Med. Chem.*, 12:1643 (2004)). As GHB is metabolized to GABA through oxidation of the alcohol of GHB followed by transamination (Doherty et al, *Biochem. Pharmacol.* 24:469 (1975)), it was considered that its removal would slow this metabolic pathway, but it was recently showed that GHB-ethers (4-6) (FIG. 2) have lower affinity than GHB at GHB receptors (Carter et al, *J. Pharmacol. Exp. Ther.*, 313:1314 (2005)). One important finding was that 3-hydroxyphenylacetic acid has greater affinity than GHB for GHB receptors, and displaces [$^3$H]GABA by 44% from $GABA_A$ receptors at 1 mM (see Table 1) (Carter et al, *J. Pharmacol. Exp. Ther.*, 313: 1314 (2005)).

Applicants investigated the introduction of ethers onto the 3-hydroxyl of 3-hydroxyphenylacetic acid in order to compare ethers of 3-hydroxyphenylacetic acid with the 4-ethers of GHB, and to determine if the removal of the hydrogen bond donating hydroxyl group reduced the affinity at $GABA_A$ receptors.

BRIEF DESCRIPTION OF THE SEVERAL VIEW OF THE DRAWINGS

Figure 1:
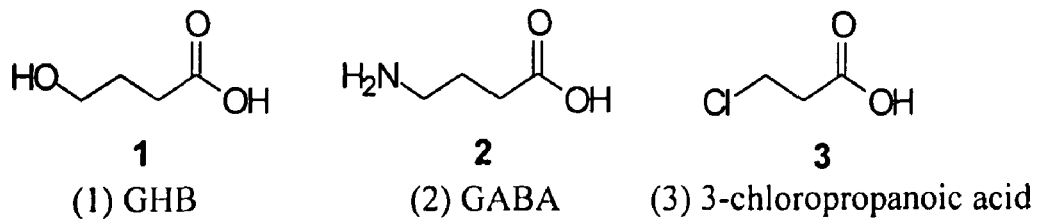
FIG. 1 shows the chemical structures of GHB (1), GABA (2) and 3-chloropropanoic acid (3).
Figure 2:
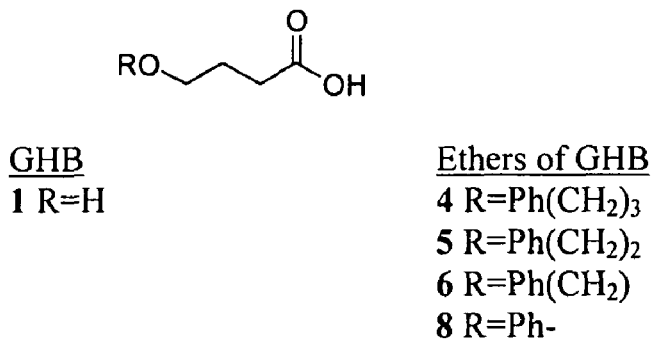
FIG. 2 shows the chemical structures of GHB (1) and ethers of GHB (4-6 and 8).
Figure 3:
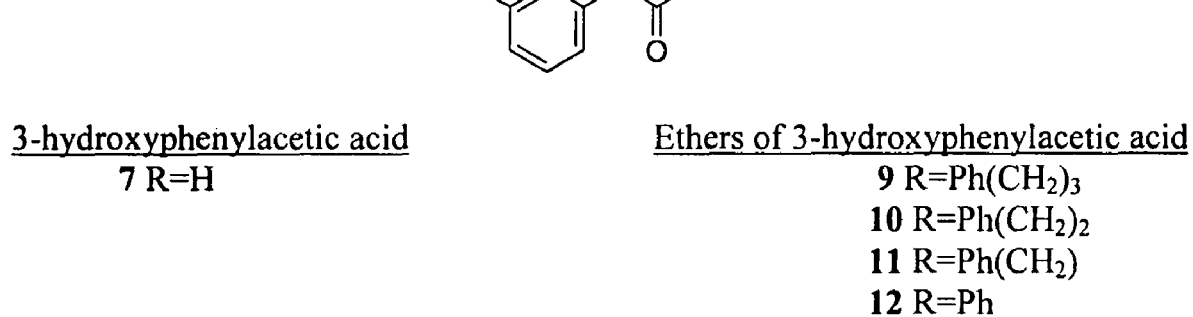
FIG. 3 shows the chemical structures of 3-hydroxyphenylacetic acid (7) and ethers of 3-hydroxyphenylacetic acid (9-12).
Figure 4:
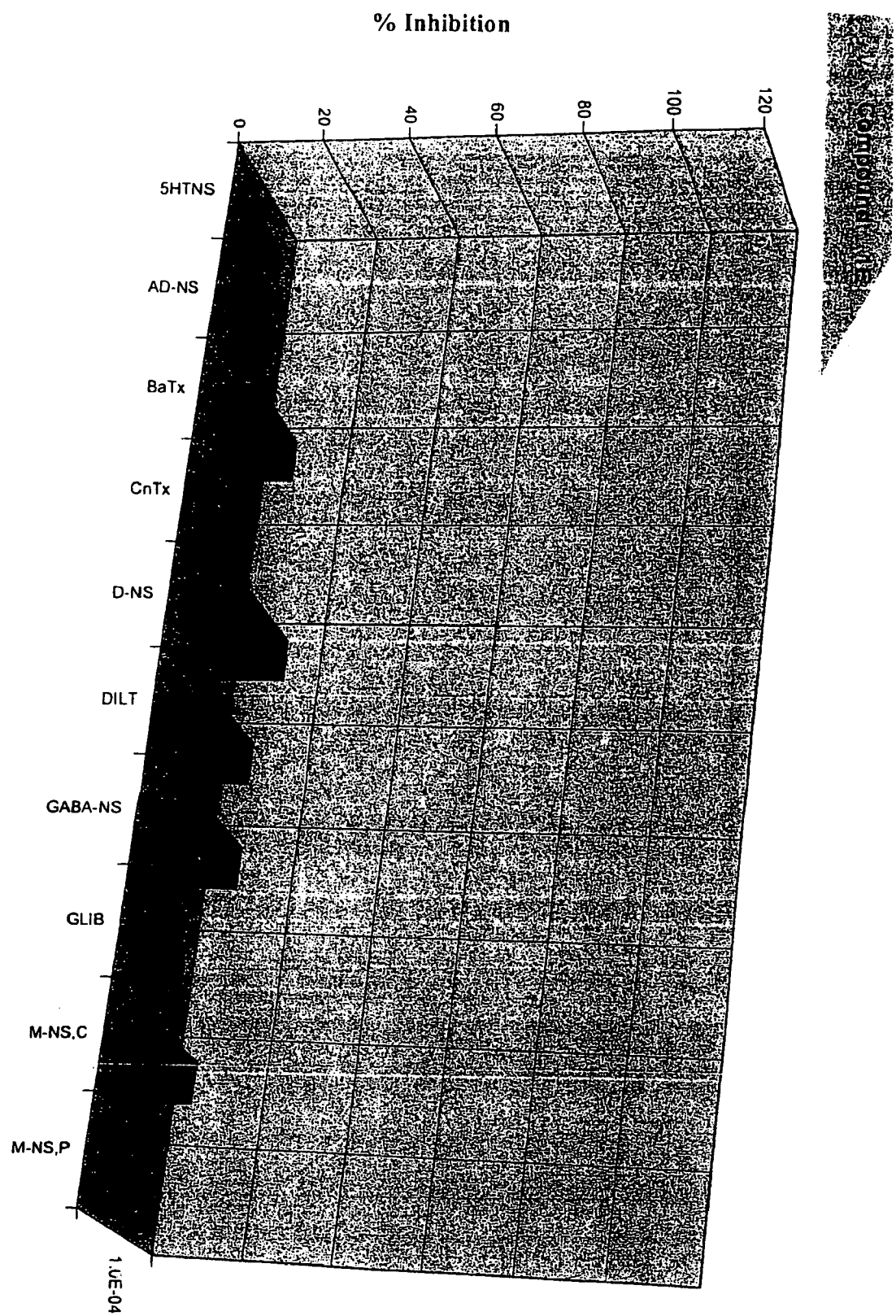

FIG. 4 the shows the test data of Table 1 in graph form.

DETAILED DESCRIPTION OF THE INVENTION

The ethers of 3-hydroxyphenylacetic acid have the chemical structural shown in formula (I):

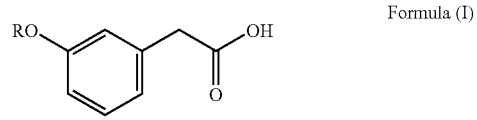

Formula (I)

where R is an aromatic group or arylalkyl substituent.

The aromatic group may be any aromatic group. Non-limiting examples are mono- and polycyclic aromatic carbocycles (such as phenyl and naphthyl) and mono- and bicyclic aromatic heterocycles, including, for example, oxygen, sulfur and nitrogen containing heterocyclic groups (such as pyridyl, furanyl, and bezofuranyl). The aromatic group may be substituted or unsubstituted.

The alkyl moiety in the arylalkyl substituent may be any alkyl group. Non-limiting examples of the alkyl moiety in the arylalkyl substituent are linear or branched, substituted or unsubstituted alkyl groups. Non-limiting examples of the alkyl moiety in the arylalkyl substituent may contain from 1 to 20 carbon atoms, preferably 1 to 10 carbon atoms, preferably 1 to 3 carbon atoms. The aryl group in the arylalkyl substituent may be any aryl group, including containing heteroaryls, such as heteroaryl groups containing oxygen, sulfur and nitrogen. The aryl group may be substituted or unsubstituted. Non-limiting examples of the aryl group are phenyl (Ph), naphthyl, furanyl, benzofuranyl and pyridyl.

Non-limiting examples of R are Ph, $Ph(CH_2)_3$—, $Ph(CH_2)_2$—, and $Ph(CH_2)$—.

Non-limiting examples of ethers of 3-hydroxyphenylacetic acid are:

The phenylpropyl ether of 3-hydroxyphenylacetic acid (9);

The phenethyl ether of 3-hydroxyphenylacetic acid (10); and

The phenyl ether of 3-hydroxyphenylacetic acid (12).

The ethers of 3-hydroxyphenylacetic acid of the present invention may be used for the same types of therapeutic treatments as GHB. The ethers of 3-hydroxyphenylacetic acid may be used as GHB receptor-selective ligands which can be used for any activity which occurs through GHB sites.

The ethers of 3-hydroxyphenylacetic acid of the present invention may be used for treatment of symptoms of fibromyalgia or chronic fatigue syndrome. Patients with fibromyalgia, also referred to as fibromyalgia syndrome, FMS or fibrositis syndrome, report widespread musculoskeletal pain, chronic fatigue, and non-restorative sleep, and show specific regions of localized tenderness in the absence of demonstrable anatomic or biochemical pathology. Typically, they describe light and/or restless sleep. They awaken feeling unrefreshed with pain, stiffness, physical exhaustion, and lethargy. See, for example, U.S. Pat. No. 5,990,162 and Moldofsky et al., *J. Muscoloskel. Pain*, 1:49 (1993).

The ethers of 3-hydroxyphenylacetic acid of the present invention may be used for treatment of narcolepsy and sleep disorders, including daytime sleepiness, cataplexy, sleep paralysis and hypnagogic hallucinations. See, for example, U.S. Pat. No. 6,472,431, U.S. Pat. No. 6,623,730, Scharf, *Sleep*, 21:507-514 (1998), and University of Texas, *Narcolepsy drug relieves pain, improves sleep in fibromyalgia syndrome patients, study finds, HSCNEWS*, vol. XXXVIII, Issue 47 (Nov. 22, 2005).

The ethers of 3-hydroxyphenylacetic acid of the present invention may be used for treatment of alcohol addiction and withdrawal, including alcoholism, alcohol withdrawal symptoms and alcohol abstinence syndrome in patients. See, for example, U.S. Pat. No. 4,983,632, U.S. Pat. No. 6,436,998, U.S. Pat. No. 6,472,431, U.S. Pat. No. 6,623,730, and U.S. Pat. No. 6,770,784.

The ethers of 3-hydroxyphenylacetic acid of the present invention may be used for treatment drug addiction and withdrawal, including opiate withdrawal, including both heroin and methadone withdrawal and morphine, cocaine, and psychoactive drugs. See, for example, U.S. Pat. No. 5,426,120, U.S. Pat. No. 6,436,998, U.S. Pat. No. 6,472,431, and U.S. Pat. No. 6,770,784.

Other contemplated uses for the ethers of 3-hydroxyphenylacetic acid of the present invention include, but are not limited to:

Reducing sleep apnea. See, for example, U.S. Pat. No. 6,472,431;

As an anesthesia and for long-term sedation. See, for example, U.S. Pat. No. 6,623,730, U.S. Pat. No. 6,472,431, and U.S. Pat. No. 5,380,937;

For analgesic effects and as a pain reliever. See, for example, U.S. Pat. No. 6,472,431;

For closed cranio-cerebral trauma and as a soporific. See, for example, U.S. Pat. No. 5,380,937; and to reduce intracranial pressure in patients. See, for example, U.S. Pat. No. 6,472,431;

To increase growth hormone levels in patients and to stimulate growth hormone and prolactin production. See, for example, U.S. Pat. No. 5,840,331 and U.S. Pat. No. 6,472,431;

As a narcotic in patients. See, for example, U.S. Pat. No. 6,472,431;

As an anorectic, to heighten sexual desire, to produce pleasurable effects such as euphoria and as for smooth muscle relaxation. See, for example, U.S. Pat. No. 6,623,730;

To treat patients with chronic schizophrenia characterized by autism, inactivity, and apathy; catatonic schizophrenia; chronic schizophrenia with hallucination and delusion; atypical psychoses; and chronic brain syndrome due to trauma, as well as neurotic patients. See, for example, U.S. Pat. No. 6,623,730;

To relieve anxiety, tremor, and muscle rigidity in patients with Parkinson's disease. See, for example, U.S. Pat. No. 6,623,730;

For anti-ulcer activity against ulcers induced by indomethacin, restraint stress or pyloric ligation. See, for example, U.S. Pat. No. 6,623,730;

As an anti-angiogenesis agent. See, for example, U.S. Pat. No. 6,623,730;

To prevent heart damage after acute blood loss. See, for example, U.S. Pat. No. 6,623,730;

Administered prophylactically to reduce inflammation or ischemic or reperfusion injury during surgery. See, for example, U.S. Pat. No. 6,623,730; and To prevent the proliferation of cancer and functions as an antineoplastic agent; To reduce angiogenesis induced by certain types of cancer cells. For the treatment of lung cancer patients during and after surgery (attributed to the antihypoxic effects of GHB). See, for example, U.S. Pat. No. 6,623,730.

The selectivity of the compounds of the present invention may also prove useful for studying the biology of GHB receptors, free from GABAergic effects. Compounds that do not have substantial GABAergic effects are useful in studying GHB alone. For example, GHB receptors may be tested for the amount of GHB activity alone, without GABAergic effects, by administration of a compound of the present invention and measuring the affinity for GHB by a suitable method. For example, affinities may be measured through [$^3$H]NCS-382 displacement assays as described in Wu et al, *J. Pharmacol. Exp. Ther.*, 305:675 (2003); Carter et al, *J Pharmacol. Exp. Ther.*, 313:1314 (2005); and Mehta et al, *Pharmacol. Exp. Ther.*, 299:1148 (2001). Ethers of 3-hydroxyphenylacetic acids may be prepared through dialkylation of 3-hydroxyphenylacetic acid with the relevant arylalkyl halide, followed by hydrolysis of the ester with NaOH.

The compounds of the present invention may also be salts 3-hydroxyphenylacetic acids. As used herein, the term ethers of 3-hydroxyphenylacetic acids includes salts thereof. The salts may be any salt, for example but not limited to, alkali metal (e.g. sodium, lithium or potassium) salts, alkaline earth metal (e.g. calcium or magnesium) salts, ammonium salts, salts of pharmaceutically acceptable bases (ethanolamine, diethanolamine, piperidine, piperazine and the like), salts of basic amino acids (lysine, ornithine, citrulline and the like) and etc.

The pharmaceutical composition of the present invention may comprise a pH adjusting or buffering agent. Such agents may be acids, bases, or combinations thereof. The acid may be an organic acid or an inorganic acids. The pH adjusting agent may be a mixture of more than one acid and/or more than one base, including a weak acid and its conjugate base are used to form a buffering agent.

The pharmaceutical composition of the present invention may comprise an inert substances added as diluents or vehicles or to give form or consistency when the remedy is in a solid form, though they may be contained in liquid form preparations, e.g. syrups, aromatic powders, honey, and various elixirs. Other additives include a preservative, an antioxidants, a flavoring agent, salts, excipients. Additives that may be used with the compositions of the present invention are known in the art, (see for example, "Remington's Pharmaceutical Sciences", 8th and 15th Editions, and Nema et al, 1997, which are incorporated herein in their entirety).

The compositions may be given orally in solid or liquid dosage forms, injected in a suitable vehicle, or inhaled via use of a suitable inhalation device. The compositions may be aqueous compositions. The amount of therapeutically active compounds that are administered and the dosage regimen with the compounds and/or compositions of this invention may be determined by one skilled in the art depending on a variety of factors, including the age, weight, sex and medical condition of the subject, the severity of the disease, the route and frequency of administration, and the particular compound employed.

EXAMPLE 1

Compounds 8 and 12 were purchased from Sigma-Aldrich. Compounds 9-11 were made as described above. All five compounds were assayed in their acid forms. All compounds gave satisfactory NMR (500 MHz), MS (LCMS, negative ion mode), and CHN (Atlantic Microlabs) data. (Compound 11 has been previously reported. Renaud et al, *J. Med. Chem.* 48:364 (2005) (Published on the Web Dec. 22, 2004)). Affinities were studied through [$^3$H]NCS-382 displacement assays as described in Wu et al, *J. Pharmacol. Exp. Ther.,* 305:675 (2003); Carter et al, *J. Pharmacol. Exp. Ther.,* 313:1314 (2005); and Mehta et al, *Pharmacol. Exp. Ther.,* 299:1148 (2001). Table 1 shows the $IC_{50}$ values for GHB and its analog acids using [$^3$H]NCS-382 (16 Nm) as a radioligand in rat cerebrocortical membranes, and inhibition of [$^3$H]GABA (10 Nm) binding to $GABA_A$ and $GABA_B$ receptors in rat membranes from cerebral cortex and cerebellum, respectively by the ligands at a concentration of 1 Mm. Each value is the mean±S.E.M. of at least three individual experiments performed in triplicate.

TABLE 1

| Compound | [$^3$H]NCS382 $IC_{50}$ (μM) GHB sites | Percent displacement of [$^3$H]GABA at 1 Mm | |
|---|---|---|---|
| | | $GABA_A$ | $GABA_B$ |
| 1 (GHB)[a] Comparative | 25.0 ± 1.8 | 35.5 ± 3.7 | 41.1 ± 3.1 |
| 7[a] Comparative | 12.0 ± 5.5 | 44.2 ± 2.0 | 14.0 ± 4.0 |
| 8 Comparative | 210 ± 62 | 6.3 ± 1.7 | 6.5 ± 1.0 |
| 9 (UMB109) Inventive | 4.5 ± 1.9 | 17.4 ± 13.2 | 6.0 ± 2.6 |
| 10 (UMB108) Inventive | 8.3 ± 1.6 | 15.1 ± 7.5 | -1.2 ± 7.3 |
| 11 Inventive | 46.0 ± 10 | 11.0 ± 6.2 | -4.7 ± 4.7 |

TABLE 1-continued

| Compound | [$^3$H]NCS382 $IC_{50}$ (μM) GHB sites | Percent displacement of [$^3$H]GABA at 1 Mm | |
|---|---|---|---|
| | | $GABA_A$ | $GABA_B$ |
| 12 (UMB119) Inventive | 16.3 ± 0.8 | 2.7 ± 0.5 | -5.5 ± 1.2 |

[a]Data from Carter et al, J. Pharmacol. Exp. Ther., 313: 1314 (2005).

EXAMPLE 2

GHB (Compound 1) and 3-hydroxyphenylacetic acid (Compound 7) have affinity for GHB receptors and displace [$^3$H]NCS382 binding with $IC_{50}$ values of 25 μM and 12 μM, respectively. Importantly, both compounds also have weak affinity for GABA receptors. The introduction of a phenyl ether into GHB (Compound 8) yielded a compound with an affinity of 210 μM at GHB receptors, consistent with results obtained with other ethers of GHB, including the benzyl ether (Compound 6), phenethyl ether (Compound 5), and phenylpropyl ether (Compound 4), all of which have affinities at GHB sites an order of magnitude lower than GHB. In contrast, for ethers of 3-hydroxyphenylacetic acid, the marked decreases in GHB affinity were not observed and, in the case of the phenylpropyl ether of 3-hydroxyphenylacetic acid (Compound 9), GHB receptor affinity increased slightly, while displacement of [$^3$H]GABA from GABA receptors decreased. The phenethyl ether of 3-hydroxyphenylacetic acid (Compound 10) and the phenyl ether of 3-hydroxyphenylacetic acid (Compound 12) have a similar affinity as 3-hydroxyphenylacetic acid at GHB receptors, but with decreased affinity at GABA receptors. The benzyl ether of 3-hydroxyphenylacetic acid (Compound 11) had 4-fold lower affinity for GHB receptors than 3-hydroxyphenylacetic acid, but displaced GABA to a lower extent than 3-hydroxyphenylacetic acid. The phenethyl ether of 3-hydroxyphenylacetic acid (Compound 10), the phenylpropyl ether of 3-hydroxyphenylacetic acid (Compound 9), and the phenyl ether of 3-hydroxyphenylacetic acid (Compound 12) having relatively high affinity at GHB receptors, and lower affinity at GABA receptors than 3-hydroxyphenylacetic acid, suggests that the aromatic group in these ethers occupies a site which is favorable for affinity at GHB receptors, but which is unfavorable for affinity at GABA receptors.

The phenethyl ether of 3-hydroxyphenylacetic acid (Compound 10) was also shown to be selective (>100-fold) for GHB receptors over other sites, including the following: adenosine, adrenergic, dopamine, GABA, melatonin, muscarinic, opioid, serotonin, and sigma receptors, and calcium, potassium, sodium, and chloride channels. Table 2 shows the test data for Compound 10 (1 compound, two replicates). Table 3 shows the percent inhibition. The testing was performed by NovaScreen Biosciences Corp. The methodology may be found at "www.novascreen.com/allassay.asp", which is herein incorporated by reference. Novascreen's assays are designed to test for inhibition of binding or enzyme activity.

For the data in the Tables, in most assays, the standard baseline range runs from −20% to +20% inhibition of binding or enzyme activity. Compounds showing results in this range are considered inactive at this site. Compounds which show inhibition in the range of 20% to 49% are considered to show marginal activity at the receptor site. A criteria of 50% inhibition (or greater) was used to qualify a compound as active. Active compounds tested at multiple concentrations can generally be expected to show a dose-dependent response.

The ethers of 3-hydroxyphenylacetic acid of the present invention show high affinity GHB receptors and are selective ligands for GHB receptors, no significant affinity at GABA receptors, and are not expected to be rapidly metabolized to GABAergic ligands. The displacement of [$^3$H]GABA is at least less than 30% displacement of [$^3$H]GABA at 1 mM. More preferably, the displacement of [$^3$H]GABA may be at least less than about 20% displacement of [$^3$H]GABA at 1 mM. The displacement of [$^3$H]GABA may be at least less than about 10% displacement of [$^3$H]GABA at 1 mM.

TABLE 3-continued

Solubility of Stock: Soluble

| Receptor | Percent Inhibition (Average; N = 2) 1.0E−4 |
|---|---|
| Melatonin, Non-selective | 12.69% |
| Muscarinic, Non-selective, Central | 6.98% |
| Muscarinic, Non-selective, Peripheral | −0.77% |
| Opiod, Non-selective | 0.09% |
| Serotonin, Non-selective | −1.83% |
| Sigma, Non-selective | 4.30% |
| ION CHANNELS | |
| Calcium Channel, Type L (Benzothiazepine Site) | 9.41% |
| Calcium Channel, Type L (Dihydropyridine Site) | 14.52% |
| Calcium Channel, Type N | −2.31% |
| GABA, Chloride, TBOB Site | −15.01% |
| Potassium Channel, ATP-Sensitive | 0.73% |

TABLE 2

Concentrations: 1.0E−4

| Assay | Assay Abbr. | Radioligand | Kd (M) | Reference Compound | Ki (M) Ref. Cpd. | Activity |
|---|---|---|---|---|---|---|
| NEUROTRANSMITTER RELATED | | | | | | |
| Aderosine, Non-selective | AD-NS | [3H]NECA | 7.7E−9 | Neca | 7.64E−9 | No |
| Adrenergic, Alpha 1. Non-selective | a1-NS | [3H]7-MeOxy-Prazosin | 2.0E−10 | Phentolamine | 3.62E−9 | No |
| Adrenergic, Alpha 2. Non-selective | a2-NS | [3H]RX 821002 | 1.5E−9 | Phentolamine | 9.40E−9 | No |
| Adrenergic, Beta, Non-selective | b-NS | [3H]DHA | 1.74E−4 | Alprenolol HCl | 3.33E−9 | No |
| Dopamine, Non-selective | D-NS | [3H]Spiperone | 0.7E−9 | Spiperone HCl | 1.11E−9 | No |
| GABA, Non-Selective | GABA-NS | 3H-GABA | 1E−8 | GABA | 1.10E−8 | No |
| Melatonin, Non-selective | MEL | [125I]-2-Iodomelatonin | 66E−12 | 2-Iodomelatonin | 9.37E−11 | No |
| Muscarinic, Nan-selective, Central | M-NS, C | [3H]QNB | 1.0E−10 | Atropine sulfate | 1.26E−10 | No |
| Muscarinic, Non-selective, Peripheral | M-NS, P | [3H]QNB | 0.3E−9 | Atropine sulfate | 5.80E−10 | No |
| Opio d, Non-selective | OP-NS | [3H]Naloxone | 2.0E−9 | Naloxone HCl | 3.15E−9 | No |
| Sero onin, Non-selective | 5HTNS | [3H] LSD | 7.2E−9 | Methysergide maleate | 4.76E−9 | No |
| Sigma, Non-selective | S-NS | [3H]DTG | 3.92E−8 | Haloperidol | 2.02E−8 | No |
| ON CHANNELS | | | | | | |
| Calcium Channel, Type L (Benzothiazepine Site) | DILT | [3H] Diltiazem, cis(+) | 3.4E−8 | Diltiazem HCl | 4.40E−8 | No |
| Calcium Channel, Type L (Dihydropyridine Site) | NITR | [3H]Nitrendipine | 0.20E−9 | Nifedipine | 5.97E−10 | No |
| Calcium Channel, Type N | CnTx | [125I]-Conotoxin GVIA | 1.0E−11 | w-Conotoxin GVIA | 3.16E−11 | No |
| GABA, Chloride, TBOB Site | TBOB | [3H]TBOB | 4.5E−8 | TBPS | 2.81E−8 | No |
| Potassium Channel, ATP-Sensitive | GLIB | [3H]Glibenclamide | 0.25E−9 | Glibenclamide | 3.67E−10 | No |
| Potassium Channel, I[Kr] (hERG) (hr) | hERG | [3H]Astemizole | 100E−9 | Terfenadine | 1.55E−6 | No |
| Sodium, Site 2 | BaTx | [3H]Batrachotoxin A 20-a-Benzo | 32.0E−9 | Aconitine | 6.67E−7 | No |

Activity = greater than or equal to 50% Inhibition of binding. Refer to following page(s) for activity summary.
See Short Assay Protocol Boot for more detailed assay Information.

TABLE 3

Solubility of Stock: Soluble

| Receptor | Percent Inhibition (Average; N = 2) 1.0E−4 |
|---|---|
| NEUROTRANSMIITER RELATED | |
| Adenosine, Non-selective | −3.45% |
| Adrenergic, Alpha 1, Non-selective | −10.77% |
| Adrenergic, Alpha 2, Non-selective | 0.21% |
| Adrenergic, Beta, Non-selective | 43.67% |
| Dopamine, Non-selective | 14.51% |
| GABA, Non-Selective | 10.28% |

TABLE 3-continued

Solubility of Stock: Soluble

| Receptor | Percent Inhibition (Average; N = 2) 1.0E−4 |
|---|---|
| Potassium Channel, I[Kr] (hERG) (hr) | −11.94% |
| Sodium, Site 2 | 10.18% |

Values are expressed as the percent inhibition of specific binding and represent the average of replicate tube at each of the concentrations tested.

The references and patents cited herein are hereby incorporated by reference in their entirety.

What is claimed is:

1. A composition comprising: a compound having the chemical structural of formula (I):

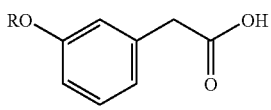

where R is an arylalkyl substituent and wherein the compound is selected from the group consisting of the phenylpropyl ether of 3-hydroxyphenylacetic acid and the phenylethyl ether of 3-hydroxyphenylacetic acid; and a pharmaceutically acceptable carrier.

* * * * *

UNITED STATES PATENT AND TRADEMARK OFFICE
CERTIFICATE OF CORRECTION

PATENT NO.       : 7,838,556 B2                                        Page 1 of 1
APPLICATION NO.  : 11/707120
DATED            : November 23, 2010
INVENTOR(S)      : Andrew Coop, Maharaj K. Ticku and Charles P. France It is certified that error appears in the above-identified patent and that said Letters Patent is hereby corrected as shown below:

Please delete the paragraph at column 1, lines 16-20 and insert therefore
--This invention was made with government support under Grant Number DA014986 awarded by the National Institutes of Health. The government has certain rights in the invention.--

Signed and Sealed this
Seventeenth Day of May, 2011

David J. Kappos
*Director of the United States Patent and Trademark Office*